US006309601B1

(12) United States Patent
Juncosa et al.

(10) Patent No.: US 6,309,601 B1
(45) Date of Patent: *Oct. 30, 2001

(54) SCANNING OPTICAL DETECTION SYSTEM

(75) Inventors: Robert D. Juncosa, Mission Viejo; William F. Butler, Carlsbad; Lei Wu, San Diego, all of CA (US); Robert H. Cormack, Boulder, CO (US)

(73) Assignee: Nanogen, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/846,876

(22) Filed: May 1, 1997

Related U.S. Application Data

(63) Continuation-in-part of application No. 08/304,657, filed on Sep. 9, 1994, now Pat. No. 5,632,957, which is a continuation-in-part of application No. 08/271,882, filed on Jul. 7, 1994, now Pat. No. 6,017,969, which is a continuation-in-part of application No. 08/146,504, filed on Nov. 1, 1993, now Pat. No. 5,605,662.

(51) Int. Cl.[7] ............ G01N 15/00; G01N 1/00; G01N 33/53; C12Q 1/68
(52) U.S. Cl. ............ 422/68.1; 422/50; 422/69; 422/82.05; 422/82.08; 422/82.09; 435/6; 435/7.1; 436/501
(58) Field of Search ............ 422/50, 68.1, 69, 422/82.05, 82.08, 82.09; 435/6, 7.1; 436/501; 935/77, 78, 88

(56) References Cited

U.S. PATENT DOCUMENTS

| 4,555,731 | 11/1985 | Zinchuk | 358/209 |
|---|---|---|---|
| 4,572,668 | 2/1986 | Auth | 356/318 |
| 4,707,235 | 11/1987 | Englert et al. | 204/182.8 |
| 4,881,812 | 11/1989 | Ohkubo et al. | 356/344 |
| 5,096,807 | 3/1992 | Leaback | 435/6 |
| 5,192,980 | 3/1993 | Dixon et al. | 356/326 |
| 5,296,703 | 3/1994 | Tsien | 250/235 |
| 5,324,401 | 6/1994 | Yueng et al. | 204/180.1 |
| 5,381,224 | 1/1995 | Dixon et al. | 356/72 |
| 5,578,832 | 11/1996 | Trulson et al. | 250/458.1 |
| 5,631,734 | 5/1997 | Stern et al. | 356/317 |

OTHER PUBLICATIONS

"Theory and Practice of Scanning Optical Microscopy", Tony Wilson and Colin Sheppard, Academic Press, 1984 (ISBN–0–12–757760–2).
Scanning Laser Microscopy Lab, Web Site print–out, http://www.science.uwaterloo.ca/research_groups/confocal (1997).

Primary Examiner—Ardin H. Marschel
(74) Attorney, Agent, or Firm—Lyon & Lyon LLP

(57) ABSTRACT

An optical detection system is adapted for detection of biological reactions. An excitation source illuminates a portion of an object to be examined, the portion preferably comprising one microlocation out of an array of microlocations. An intervening optical detection platform serves to direct the excitation radiation to the portion of the object to be illuminated. A detector receives the emitted radiation from the object to be examined, the detector being characterized in that the diameter of the region examined by the detector is the same as or smaller than the diameter of the illuminated region, and comprises less than the entire surface of the object to be examined, and most preferably images a whole or a part of a single microlocation. In operation, a microscopy system is formed in which the excitation radiation is substantially in focus at the surface of the object to be examined. In one aspect of this invention, the optical detection platform includes an excitation detector that measures reflected excitation radiation from the object to be examined. This information is compared to prestored information regarding the location of the microlocations and interstitial regions on the object to be examined, whereby alignment information is obtained. The excitation radiation may then be precisely directed to a given microlocation or portion thereof to perform the examining through the system.

34 Claims, 5 Drawing Sheets

SCANNING OPTICAL DETECTION SYSTEM

RELATED APPLICATION INFORMATION

This application is related by subject matter to application Ser. No. 08/534,454, filed Sep. 27, 1995, entitled "Apparatus and Methods for Active Programmable Matrix Devices", now issued as U.S. Pat. No. 5,849,486, which is a continuation-in-part of application Ser. No. 08/304,657, filed Sep. 9, 1994, entitled, as amended, "Molecular Biological Diagnostic Systems Including Electrodes", now, issued, as U.S. Pat. No. 5,632,957; which is a continuation-in-part of application Ser. No. 08/271,882, filed Jul. 7, 1994, entitled, as amended, "Methods for Electronic Stringency Control for Molecular Biological Analysis and Diagnostics", now issued, as U.S. Pat. No. 6,017,969, which is a continuation-in-part of application Ser. No. 08/146,504, filed Nov. 1, 1993, entitled, as amended, "Active Programmable Electronic Devices for Molecular Biological Analysis and Diagnostics", now issued as U.S. Pat. No. 5,605,662, all incorporated herein by reference as if fully set forth herein.

FIELD OF THE INVENTION

This invention relates to optical detection and examining systems, especially systems for examining fluorescent or chemilluminescent radiation. More particularly, the invention relates to optical systems for examining localized areas containing biological fluorescent materials, where those systems require relatively high sensitivity.

BACKGROUND OF THE INVENTION

Molecular biology comprises a wide variety of techniques for the analysis of nucleic acid and protein. Many of these techniques and procedures form the basis of clinical diagnostic assays and tests. These techniques include nucleic acid hybridization analysis, restriction enzyme analysis, genetic sequence analysis, and the separation and purification of nucleic acids and proteins (See, e.g., J. Sambrook, E. F. Fritsch, and T. Maniatis, *Molecular Cloning: A Laboratory Manual,* 2 Ed., Cold spring Harbor Laboratory Press, Cold Spring Harbor, N.Y., 1989).

Most of these techniques involve carrying out numerous operations (e.g., pipetting, centrifugations, electrophoresis) on a large number of samples. They are often complex and time consuming, and generally require a high degree of accuracy. Many a technique is limited in its application by a lack of sensitivity, specificity, or reproducibility. For example, these problems have limited many diagnostic applications of nucleic acid hybridization analysis.

The complete process for carrying out a DNA hybridization analysis for a genetic or infectious disease is very involved. Broadly speaking, the complete process may be divided into a number of steps and substeps, broadly including the steps of obtaining the sample, disrupting the cells within the sample, performing complexity reduction or amplification, performing some sort of assay or hybridization, followed by detection of the presence or absence of a desired event serving to generate a result.

New techniques are being developed for carrying cut multiple sample nucleic acid hybridization analysis on micro-formatted multiplex or matrix devices (e.g., DNA chips) (see M. Baringa, 253 Science, pp. 1489, 1991; W. Bains, 10 Bio/Technology, pp. 757–758, 1992). These methods usually attach specific DNA sequences to very small specific areas of a solid support, such as micro-wells of a DNA chip. These hybridization formats are micro-scale versions of the conventional "dot blot" and "sandwich" hybridization systems.

A variety of methods exist for detection and analysis of the hybridization events. Depending on the reporter group (fluorophore, enzyme, radioisotope, etc.) used to label the DNA probe, detection and analysis are carried out fluorometrically, colorimetrically, or by autoradiography. By observing and measuring emitted radiation, such as fluorescent radiation or particle emission, information may be obtained about the hybridization events. Even when detection methods have very high intrinsic sensitivity, detection of hybridization events is difficult because of the background presence of non-specifically bound materials and materials with inherent fluorescent characteristics. A number of other factors also reduce the sensitivity and selectivity of DNA hybridization assays.

In conventional fluorometric detection systems, an excitation energy of one wavelength is delivered to the region of interest and energy of a different wavelength is emitted and detected. Large scale systems, generally those having a region of interest of two millimeters or greater, have been manufactured in which the quality of the overall system is not inherently limited by the size requirements of the optical elements or the ability to place them in optical proximity to the region of interest. However, with small geometries, such as those below 2 millimeters, and especially those on the order of 500 microns or less in size of the region of interest, the conventional approaches to fluorometer design have proved inadequate. Generally, the excitation and emission optical elements must be placed close to the region of interest. Preferably, a focused spot size is relatively small, often requiring sophisticated optical designs. As the size of the feature to be observed decreases, the demands for high accuracy in mechanical alignment increase. Further, because it is usually desirable to maximize the detectable area, the size of the optical components required to achieve these goals in relation to their distance from the region of interest becomes important, and in many cases, compromises the performance obtained.

Various prior art attempts have been made to image multiple sites in immunoassay systems. In Leaback, U.S. Pat. No. 5,096,807, there is a disclosure of an imaging immunoassay detection apparatus system and method purported to be capable of detecting and quantifying multiple light-emitting reactions from small volume samples simultaneously. A plurality of individual chemical reactant samples are each capable of emitting photons when a reaction takes place. These samples are arranged in a spaced relationship with respect to each other, and a detection system is operatively positioned so as to simultaneously detect the presence and x-y location of each photon emitted from any reacting sample. One disclosed carrier is a microtiter plate with multiple samples, e.g., 96, arranged in rows and columns. Various imaging devices arc disclosed, such as an imaging photon detector, microchannel plate intensifiers and charged coupled devices (CCDs). Preferably, the signals representing the discrete areas of reactions have the background noise signal subtracted from them.

Yet other systems for imaging multiple sites in immunoassay systems utilize sequential scanning techniques. Multiple-well screening fluorometer systems move multiple sites relative to a fluorometer. Certain versions of the systems utilize a motorized stage and others arrange the samples on a wheel, which sequentially rotate samples into position for observation by the fluorometer. With these techniques, the samples are presented to the detector in a serial manner.

Another multiple location immunoassay system is disclosed in Elings et al. U.S. Pat. No. 4,537,861 entitled "Apparatus and Method for Homogeneous Immunoassay". A spatial pattern formed by a spatial array of separate regions of antiligand material are disposed on a surface. The presence or absence of a binding reaction between a ligand and the antiligand is then detected. A source of illumination is shined on the combined ligand-antiligand location, and the emitted radiation detected. The contribution to the imager due to free labeled molecules plus background contaminants are suppressed through use of a chopper system in positional correlation to the examined array which generates a reference signal.

Various microscope systems for the detection of fluorescence or chemiluminescence have been known to the art. For example, Dixon et al. U.S. Pat. No. 5,192,980 entitled "Apparatus and Method for Spatially- and Spectrally-Resolved Measurements" discloses a scanning optical microscope or mapping system for spectrally-resolved measurement of light reflected, emitted or scattered from a specimen. A confocal scanning laser microscope system is combined with a grating monochromator located in the detector arm of the system. A spectrally resolved image is generated for a given point of illumination. Spatial resolution is achieved by moving the sample on a movable stage.

Another scanning confocal microscope is disclosed in U.S. Pat. No. 5,296,703 entitled "Scanning Confocal Microscope Using Fluorescence Detection". A scanning confocal microscope is provided for scanning a sample with an incident beam of radiation and detecting the resulting fluorescence radiation to provide data suitable for use in a raster scanned display of the fluorescence. First and second closely spaced scanning mirrors direct an incident beam to a sample and direct the fluorescent radiation towards a fluorescence detection system. Spectral resolution is achieved in the detection system by utilizing a dichroic mirror which serves to separate various wavelengths which are then separately detected by photomultiplier tubes. The system additionally generates a reference beam which impinges on one of the scanning mirrors, the reflected scanning reference beam is directed through a grating and having an alternating sequence of transparent and opaque regions. The transmitted beam is detected and utilized to generate a clock signal representative of the position of the scanning reference beam. The clock signal is used to control analog-to-digital circuits in the fluorescence detection system. In this way, the sampling of the outputs of the photomultiplier tubes generates data representative of linear scans of the sample, despite the use of a scanning mirror that scans in a non-linear, sinusoidal fashion.

Despite the desirability of having an improved examining system, and the need for higher sensitivity in such systems, the systems described previously have been less than optimal. It is the object of this invention to provide an improved examining and scanning system which remedies these deficiencies.

SUMMARY OF THE INVENTION

A scanning optical detection system provides for optical and mechanical positioning, alignment and examining of a sample. A source of excitation radiation, such as a laser, supplies excitation radiation to an optical detection platform either directly, or in the preferred embodiment, through a mechanically decoupled system such as an optical path, using optics or mirrors, or most preferably through an optical fiber. The optical detection platform receives the excitation radiation, imparts a direction to the radiation, preferably through a x-y scanning system, examines the excitation radiation in the region to be examined, and detects emitted radiation from the object. The detector preferably includes a filter adapted to substantially reject, preferably greater than a factor of $10^7$, excitation radiation. The field of view of the detector, preferably a photomultiplier tube, is of a restricted size, preferably restricted through an aperture disposed at the inlet to the photomultiplier tube.

In the preferred embodiment, the system comprises a confocal microscope system in which the excitation radiation illuminates one microlocation in an array of microlocations, but not other microlocations or intervening or interstitial areas at the same time. In the preferred embodiment, the excitation radiation significantly illuminates a subset of the area comprising a microlocation. Similarly, the detector aperture is preferably sized to be of substantially the same lateral examining area as is the excitation radiation at the examined microlocation. By restricting the scope of the illumination to the area of a given microlocation, or a fraction thereof, coupled with restricting the field of view of the detector to the region of illumination, preferably through use of an aperture, significant improvements in signal-to-noise ratio may be achieved.

Improved methods of scanning utilizing a confocal optical detection system generally comprise the steps of, first, providing focused excitation energy to a region to be examined, that region comprising less than all of the region to be serially examined, second, focusing a detector on the region to be examined, the diameter of the detector aperture at the object to be examined being substantially the same as or smaller than the diameter of the object being examined, but the same as or greater than the diameter of the excitation radiation at the object to be examined, whereby the region of the object to be examined is illuminated and the detector is focused on the illuminated portion.

In one aspect of this invention, a dual detector system is utilized. A first detector is operatively positioned to receive radiation reflected from the object, preferably including the microlocations, the first detector being coupled to a position detection system for determining the position of the microlocations. A second detector is operatively positioned to receive the radiation emitted from the microlocations, such as fluorescent or chemiluminescent radiation. Such a dual detector system is advantageously used in the methods for aligning the object including the microlocations to be examined with the optical detection platform.

An alignment system is provided for aligning the optical detection platform and the object to be examined. In the preferred embodiment, an excitation radiation detector is used in combination with the scanning system and focusing optics. In the preferred method of alignment, the excitation radiation is scanned over the object to be examined, preferably through operation of the x-y positioning system, and the excitation radiation reflected from the object to be examined is made incident on the excitation detector. The output of the excitation reflectance detector, after association with the spatial coordinates available from the scanning system, can be used to extract optical information about the microlocations. If operated in a raster scanning mode, a two-dimensional image can be extracted from a single high sensitivity detector. If the microlocation pattern is known, image processing techniques can be used to precisely determine the coordinates of the microlocations to the accuracy of the scanning system, which can be much more precise than the initial positioning of the microlocation bearing device in relation to the optical detection system. Once the position of the microlocations is known, the examining and detection of a specific microlocation may then be performed.

In yet another aspect of this invention, a laser power monitor is utilized. Both short and long term fluctuations in the power level of the excitation source may be corrected. Long term changes in the power level may be compensated for by changing the sensitivity of the detector, and short term fluctuations may be compensated for by multiplication of a correction factor applied to the output of the detector.

Accordingly, it is an object of this invention to provide an optical detection system having an improved signal-to-noise ratio.

It is yet another object of this invention to provide an examining system having high sensitivity and reliability.

It is yet another object of this invention to provide a sensitive diagnostic system at a relatively low cost.

DETAILED DESCRIPTION OF THE INVENTION

Figure 1:
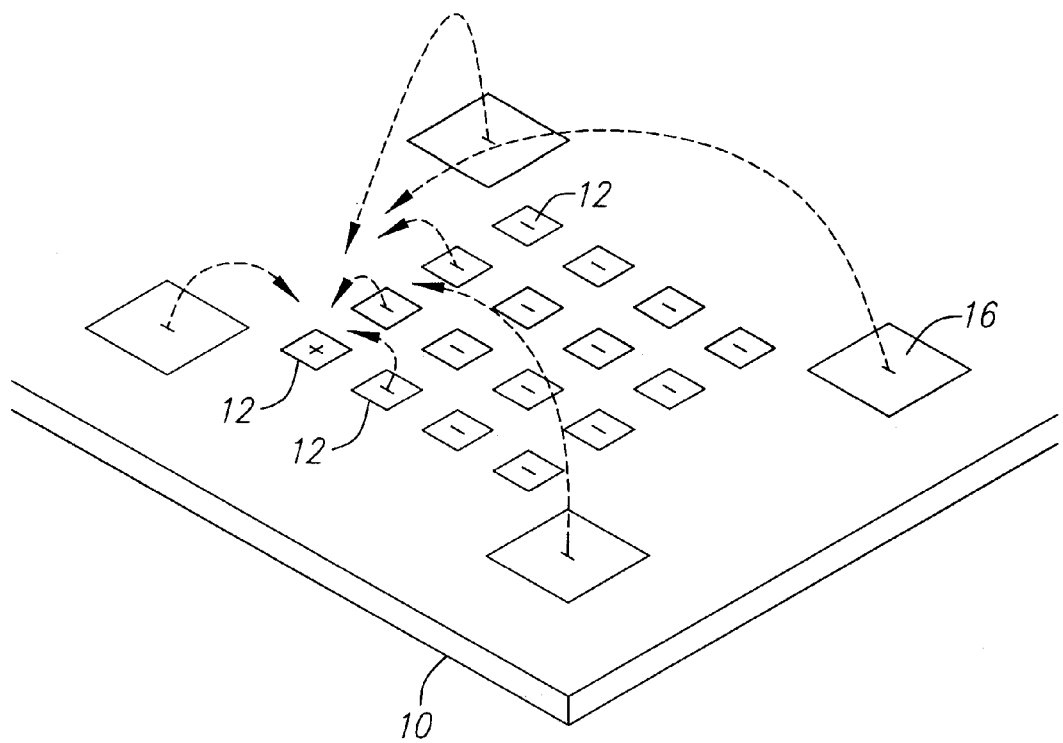
FIG. 1 shows the active, programmable matrix system in perspective view.

FIG. 1 illustrates a simplified version of the active programmable electronic matrix (APEX) hybridization system for use with this invention. Generally, a substrate 10 supports a matrix or array of electronically addressable microlocations 12. Relatively larger microlocations 16 may optionally be disposed around the smaller microlocations 12. The microlocations generally comprise those physical regions on or near the surface of the substrate 10 where some action or reaction of interest occurs, e.g., hybridization, ligand-antiligand reaction, which is later to be optically, e.g., via fluorescent or chemiluminescence, detected. In one mode of use, the active, programmable, matrix system transports charged material 14 to any of the specific microlocations 12, such as the microlocation 12 labeled "+" in FIG. 1.

A microlocation as it relates to the detection system and methods of the instant inventions is generally characterized as being a substantially two-dimensional region, the two dimensions being preferably substantially parallel to the surface of the substrate 10, the lateral extent of the microlocation typically being greater than the diffraction limited size of excitation radiation for use in the detection system. In the preferred embodiment, a microlocation has a lateral dimension which is substantially greater, e.g., 5 times greater, and more preferably, 10 times greater than the lateral dimension of a diffraction limited spot size for the excitation source at the microlocation. The microlocations may be separated by intervening or interstitial areas in which no observable reaction is intended to occur. However, microlocations need not be separated, such as in the case of contiguous microlocations.

Figure 2:
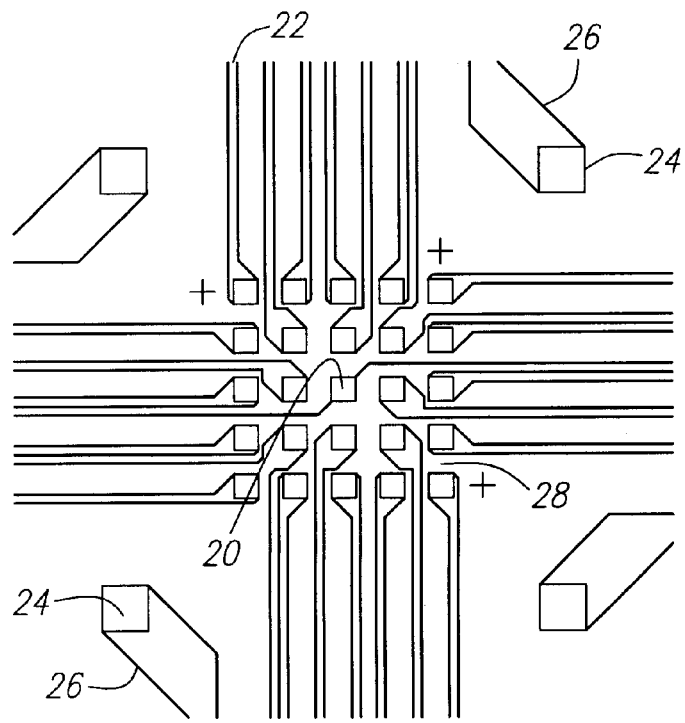
FIG. 2 shows a plan view of multiple micrelocations on an object to be examined.

FIG. 2 shows a plan view of an array of microlocations 20 to be examined. As shown, a 5×5 array of microlocations 20 is provided. While this number and arrangement of microlocations 20 is shown for convenience in FIG. 2, the number and positional arrangement of microlocations 20 relative to each other is unlimited. Leads 22 connect a microlocation 20 to a power supply. As shown in FIG. 2, multiple leads 22 may be connected to a given microlocation 20, though a single lead 22 may also be used to connect to a single microlocation 20. Electrodes 24 are disposed adjacent the array of microlocations 20 and are connected via one or more leads 26 to a power supply. As shown, the system typically includes interstitial regions 28 between the microlocations 20. The interstitial regions 28 comprise that space between the various microlocations 20 which contain the diagnostic or information bearing portions of the system. Preferably, the interstitial regions 28 are formed of material having low or reduced emission at the wavelength which corresponds to the emission wavelength, or is within the range of detection of the emission detector.

In the preferred embodiment, the array of microlocations is formed in an area nominally 1 cm×1 cm. In the embodiment shown, the 5×5 array of microlocations 20 are within a 2 mm×2 mm region. An individual microlocation 20 may be of various diameters and shapes, but is preferably less than $100\mu$ in diameter with the preferred shape being round. In the preferred embodiment, the excitation beam and microlocation are both round.

Figure 3:
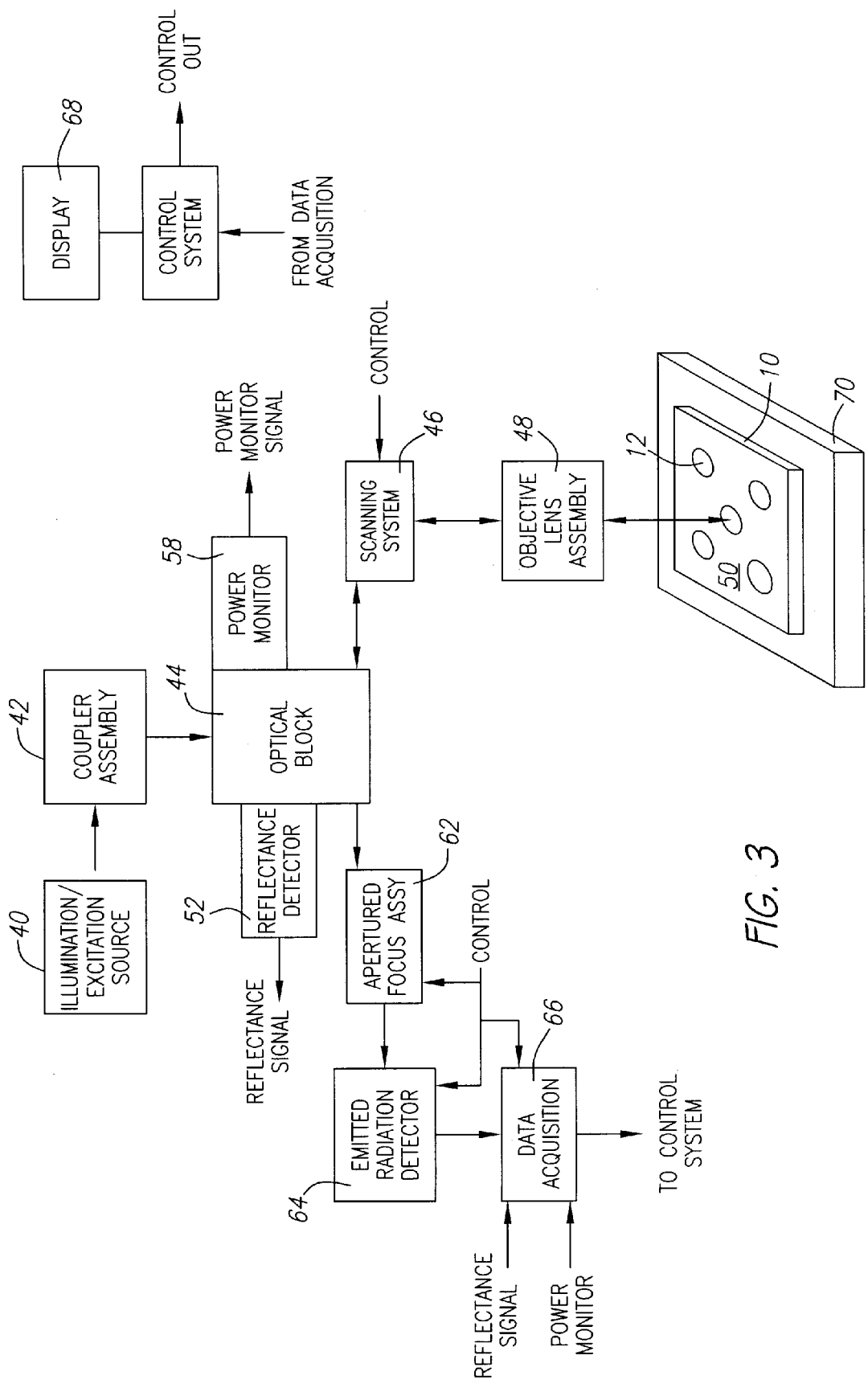
FIG. 3 shows a block diagram of the system.

FIG. 3 shows a block diagram view of the optic al components of the system in association with a perspective view of an object bearing multiple microlocations to be examined. An illumination, excitation source 40, preferably a laser, provides radiation via a coupler assembly 42 to an optical block 44. The optical block 44 passes the radiation from the source 40 to the scanning system 46, which directs the radiation via objective lens assembly 48 towards the object to be examined 50, which includes microlocations 12 disposed on a substrate 10. Light reflected from the object 50 including the microlocations 12 retraces through the objective lens assembly 48, the scanning system 46 and enters the optic al block 44, where upon the reflectance detector 52 generates a reflectance signal 54 which is provided to the data acquisition system 66. Optionally, a power monitor 58 generates a monitoring signal 60, which constitutes a signal indicative of the power of the source 40. The power monitoring signal 60 is provides to the data acquisition system 66.

Radiation from the excitation source 40 incident upon a microlocation 12 via the optical block 44 and scanning system 46 may, given a detectable condition, generate a detectable signal, such as a fluorescent or chemiluminescent radiation. Such emitted radiation passes via the scanning system 46 to the optical block 44 and to the aperture and focus assembly 62, and the emitted radiation detector 64. The detector 64 preferably communicates with the control system 56. The detector 64 is optionally coupled to a data acquisition unit 66. Further, a display 68 may be utilized to provide the user with a visual display. A support 70 serves to support the substrate 10.

Figure 4:
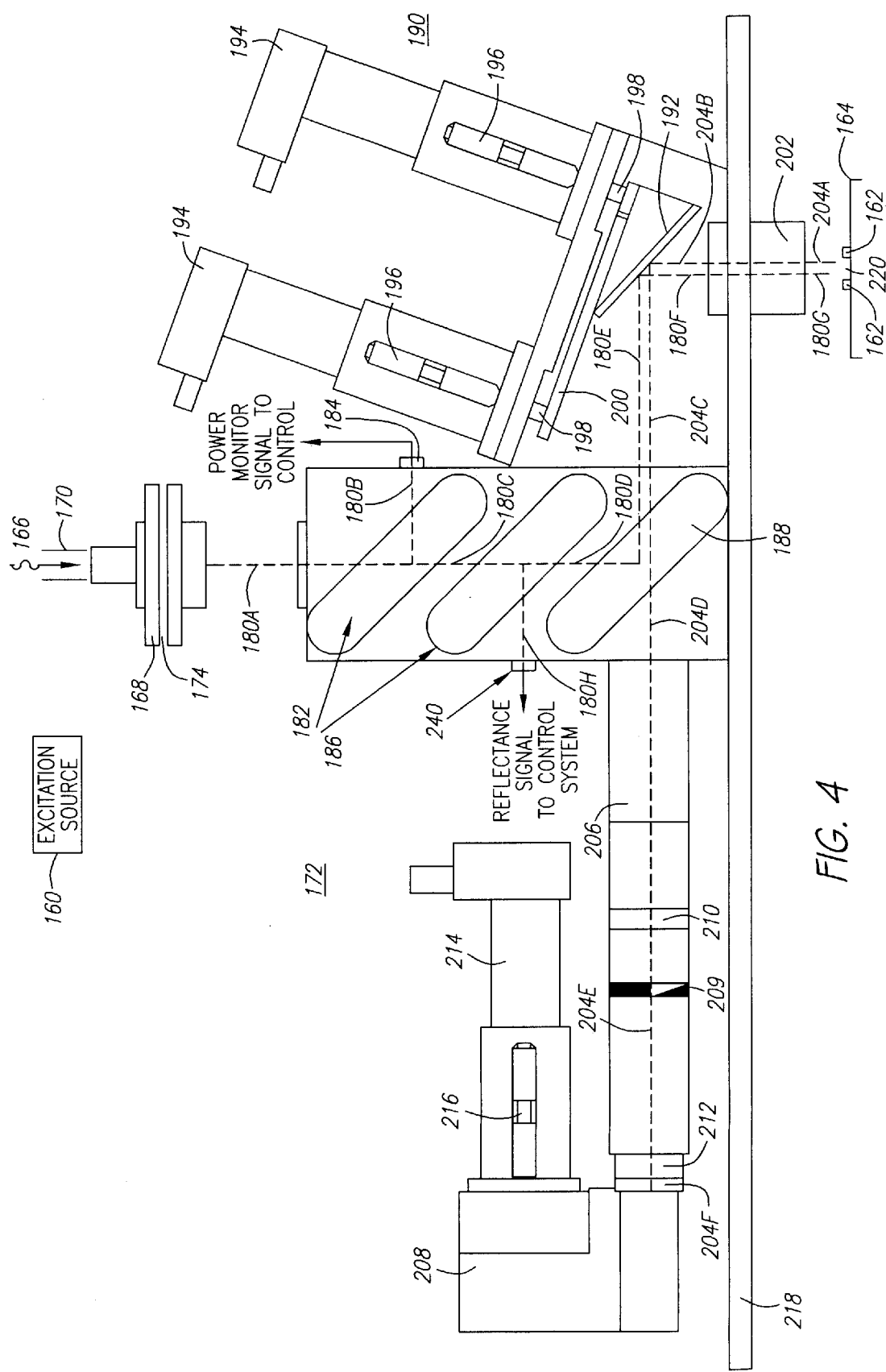
FIG. 4 shows a cross-sectional view of the optical detection platform and associated structures.

FIG. 4 shows a cross-sectional view of the optical detection platform and associated devices. An excitation source 160 provides illumination for the system. In the preferred embodiment, a single laser source is used. While the excitation wavelength depends on the fluorophore, chromophore or other material to be excited, the preferred wavelength is 594 nm. Preferably, the diameter of the beam when incident on the surface 164 of the object to be examined is smaller than a given microlocation 162 (not to scale in FIG. 4).

When the diameter of a beam is referred to, various standards are known to the art for such a determination, such as the relative intensity falling to $e^{-2}$. For an APEX type device, the diameter of the beam is preferably nominal at 50 microns with the microlocations being at 80 microns. Mode structure in the laser is preferably reduced by using a single mode laser and/or a single mode optical fiber.

The light 166 is transferred from the excitation source 160 to an optional fiber coupling 168 when an optical fiber 170 is used to deliver light 166 to the optical detection platform 172. Optionally, the light 166 may also be passed through a filter 174 disposed in the optical path to eliminate spurious radiation from entering the optical detection platform 172 at a wavelength range other than that desired for excitation at the microlocation 162. Alternatively, the light 166 may be delivered to the optical detection platform 172 by other modes, whether by direct input from the excitation source or through the use of intervening optical elements and/or mirrors. Preferably, the excitation source 160 is mechanically decoupled from the optical detection platform 172. Such decoupling advantageously permits easier replacement of the excitation source 160 and provides for greater stability of the optical detection platform 172.

The excitation radiation 180*a* is supplied to the optical detection platform 172. In FIG. 4, the excitation radiation will be labeled 180*a*, 180*b*, etc. to refer to sequential portions of the optical path. Excitation radiation 180*a* is first optionally provided to a first beamsplitter 182 where a reflected fraction of the excitation radiation 180*b* is made incident on a laser power monitor 184. A transmitted portion of excitation radiation 180*c* is passed through the first beam splitter 182 and optionally transmitted through a second beam splitter 186 to provide transmitted excitation radiation 180*d*. A dichroic beam splitter 188 provides a reflected excitation radiation 180*e* towards the scanning system 190. Preferably, the dichroic beam splitter 188 is made substantially totally reflective at the excitation wavelength and transmissive at the emission wavelength from the fluorophore, chromophore, or other wavelength to be detected from the microlocation.

The scanning system 190 may be of any form of beam placement system consistent with the goals and objects of this invention. In the preferred embodiment, a two-axis, servocontrolled moveable mirror 192 imparts motion to the excitation radiation 180*e* which is incident upon mirror 192. Motors 194 in combination with alignment screws 196 actuate contacts 198 bearing upon plate 200 which in turn moves mirror 192. Motion of the mirror 192 permits the selective directing of excitation radiation 180*e* into excitation radiation 180*f* which will be directed to a given microlocation 162. The use of a single mirror 192 permits the manufacture of a relatively smaller optical detection platform 172 as compared to a multiple mirror system and eliminates spatial distortion imparted by one axis upon another. Where size constraints are imposed upon the optical detection platform 172, the single mirror 192 is preferred.

An objective lens 202 is disposed between the scanning system 190 and the object to be examined 164 and receives radiation 180*f* and directs the radiation 180*g* towards the microlocation 162. The objective lens 202 may be of any type known to those skilled in the art consistent with the goals and objects of this invention. In the preferred embodiment, the objective lens 202 is an infinity corrected microscope lens. That is a lens designed to focus a collimated beam to a point, and vice versa. The objective lens may be a commercially available microscope lens, or alternatively, constructed from one or more discrete lenses, such as those sold by Melles Griot. Optionally, the lens may be optimized as a scan lens, that is, a lens which has a linear relationship between the angle of the beam input and the position of the spot output. A relatively longer focal length scan lens permits scanning of a relatively larger area.

The primary optical path of the returning fluorescence 204 will be described, again using the convention of labeling 204*a*, 204*b*, etc. to refer to sequential portions of the optical path. The emitted radiation 204*a* from the microlocation 162 passes back, preferably, reversing the optical path of excitation radiation 180*g*, 180*f* and 180*e*. As used herein, the region to be examined may be examined by imaging, or monitoring the emission intensity or otherwise by monitoring any parameter indicative of the biological event to be assayed or detected. The emitted radiation 204*c* is incident upon the dichroic beam splitter 188, and is preferably substantially completely transmitted as emitted radiation 204*d*. Emitted radiation 204*d* passes to a detector 208, optionally through a tube 206. Detector 208 is chosen based upon the type and wavelength of emitted radiation 204 from the microlocations 162. In the case of an APEX device, where typically fluorescence is to be measured, the detector 208 is preferably a photomultiplier tube, most preferably one responsive in the range of from substantially 488 nm to substantially 800 nm. A high sensitivity, low noise photomultiplier tube is preferred. Preferably the photomultiplier tube 208 is operated in a current output mode utilizing a transconductance amplifier. Optionally, the photomultiplier tube 208 may be operated in a photon counting mode, with an integrator.

Optionally, the emitted radiation 204*d* is incident upon a filter 210 which serves to reject radiation at wavelengths which are not substantially the wavelength of the emitted radiation 204. Most particularly, the filter 210 should reject the excitation radiation 180, preferably at least by a factor of $10^7$ and more preferably by a factor of $10^{10}$. The filtered emitted radiation 204*e* is directed towards the detector 208. A receiving lens 209 serves to focus the radiation 204. Preferably, the receiving lens 209 images the illuminated spot on the object to be examined 164 onto the plane of the aperture 212.

In the preferred embodiment, an aperture 212 receives the emitted radiation 204*e*. The aperture 212 is preferably a pinhole aperture having a size such that the detector 208 receives light substantially only from a region not larger than, and preferably smaller than, the diameter of the microlocation 162. The actual aperture size depends on the magnification of the image, which is equal to the ratio of the focal lenghts of the receiving lens 209 and the objective lens 202. By way of example, if the receiving lens 209 has a focal length 3 times longer than the objective lens 202, then the microlocation 162 will be magnified 3 times at the aperture 212. If the microlocation 162 is, e.g., 80 microns, to create a 60 micron diameter field of view for the detector 208, the aperture 212 would require a diameter of 180 microns. The apparent size of the aperture 212 may be changed by moving it along the path of the emitted radiation 204. When the aperture 212 is at the focal point of the object lens 202, the aperture limits the emitted radiation 204 from the examined microlocation 162. As the aperture 212 is moved along the optic axis, the location where the focus occurs moves with respect to the microlocations on the chip. When the aperture 212 is in focus at the microlocations on the chip, a relatively sharp cut-off of light emitted from outside of the aperture occurs. If the system is not in focus, the cut-off boundary is relatively larger, similar to the effect of a larger aperture. In this case, the cut-off is relatively less sharp, dropping relatively slowly past the out of focus boundary. Further, the collection efficiency from within the aperture image area is lessened. The emitted radiation 204*f* passing from the aperture 212 is supplied to detector 208.

Optionally, a focus motor 214 moves the detector 208 and aperture 212. Movement of the aperture 212 permits optimization of the focus on the microlocations on the chip. Such an adjustment permits variations of the z position of the microlocations to be compensated for, thereby permitting more flexibility in the z axis positioning. An optional alignment screw 216 serves to align the detector 208 with the remainder of the optical detection platform 172. A base 218 is preferably employed to provide support to the various components of the optical detection platform. Light baffles or other environmental modifying barriers may be utilized as desired.

The laser power monitor 184 detects the excitation radiation 180*b*. The power monitor 184 provides a signal indicative of the power level of the excitation source 160. Both short and long term fluctuations in the power level of the excitation source 160 may be corrected as necessary for proper examining and quantitation. For example, long term changes in the power level of the excitation source 160 may be compensated for by changing the sensitivity of the detector 208, such as through changing the sensitivity of a photomultiplier tube. Short term fluctuations in the power level of the excitation source 160 may be compensated through multiplication of a correction factor applied to the output of the detector 208.

Accurate measurement of the laser power requires attention to the polarization states. While a conventional optical fiber may be utilized with a non-polarized laser, the use of a polarized laser in combination with a polarization preserving optical fiber is preferable to avoid polarization induced errors in power determinations.

Figure 5:
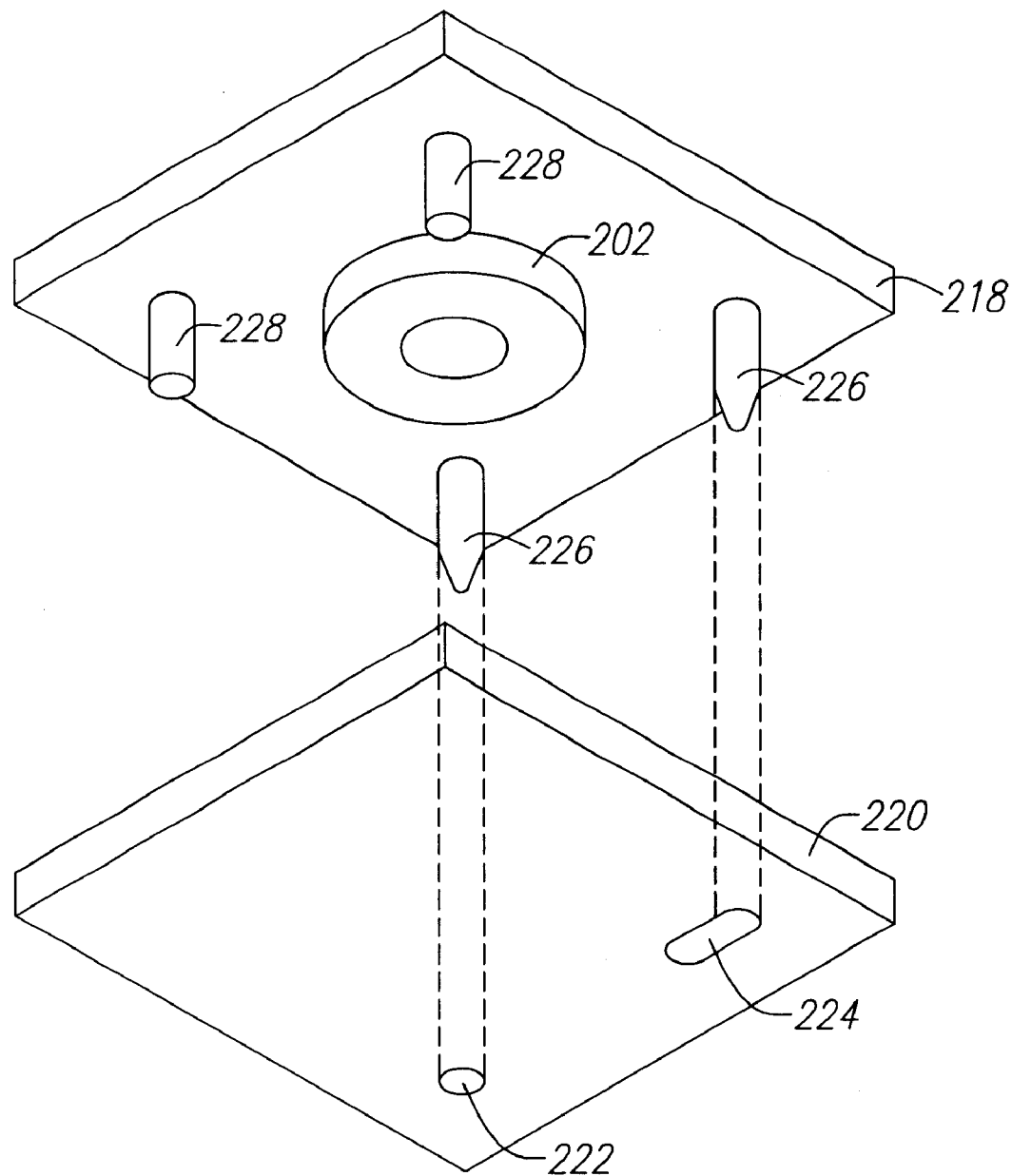
FIG. 5 shows a perspective view of the optical detection platform and associated components.

FIG. 5 shows a cross-sectional view of the relationship of the optical detection platform (shown as the base plate 218 from the underside) and the objective lens 202 in relationship to various support components and examining components. The cartridge 220 or other support for the microlocation to be examined is disposed on a support 70 (see e.g., FIG. 3) and is adapted for positioning within the field of view of the objective lens 202. In the preferred embodiment, a system is provided for mechanically positioning the cartridge 220 relative to the optical detection platform 172. Such a mechanical positioning could include a system such as shown in FIG. 5. The cartridge 220 is optionally formed with multiple location points, such as a circular detent or opening 222 and slot 224. The opening 222 and slot 224 are formed at least on the upper surface, though may be formed through the cartridge 220 as shown. One or more planar regions exist on the top of the cartridge 220. The base 218 preferably includes pointed pins 226 and at least one, and preferably two, flat pin or pins 228. The pointed pins 226 are sized to coact with the circular opening 222 and slot 224 such that the pointed section of the pointed pin 226 indexes the cartridge 220 relative to the circular opening and has latitude in the wide direction in slot 224. Additionally, the cartridge 220 may optionally be moveable in the x or y direction, preferably the y direction, to be removed from the overall system. In the preferred embodiment, a heater is utilized to maintain the cartridge 220 at the desired temperature.

In operation, a cartridge 220 is presented to the overall system, preferably moving in the y direction into general position relative to base 218. The cartridge 220 moves in the z direction, resulting in mechanical alignment of the cartridge 220 relative to the base 218 by action of the circular opening 222, slot 224 and the upper surface of the cartridge 220 in coaction with the pins 228. Such a system provides mechanical registration between the cartridge 220 and optical detection platform 172. While a relatively high degree of alignment may be achieved through such a mechanical system, the optical alignment methods described herein are advantageously utilized to provide yet a higher level of precision alignment between the optical detection platform 172 and the microlocations 220.

In operation, the optical detection platform 172 and associated components form, in the preferred embodiment, a confocal microscope system having a restricted or narrow excitation source where the diameter of the excitation source is substantially the same size or less than the diameter of a microlocation 162 (FIG. 4) in the array to be examined. The excitation radiation 180*g* is preferably in focus in the z-dimension at the microlocation 162 to be examined. The emitted radiation 204*f* to be received by the detector 208 is also of restricted or narrow aperture. Preferably the lateral diameter of the microlocation examined as emitted radiation 204*f* by the detector 208 is of substantially the same diameter as the microlocation, or more preferably less than the diameter of the microlocation 162, and most preferably substantially the same as or less than the diameter of the excitation radiation 180*g* on the microlocation 162 to be examined.

In the preferred embodiment, the combination of examining a microlocation through selective illumination by excitation radiation 180*g* to a microlocation 162, but substantially not to interstitial regions 220 (see also interstitial regions 38 in FIG. 2) and by restricting the detection of the emitted radiation 204*f* to the diameter of the microlocation, or more preferably to a diameter the same as or less than the diameter of the excitation radiation 180*g* on the microlocation 162, the signal-to-noise ratio may be increased. The sensitivity may be optimized by controlling the energy density of the excitation radiation and the intrinsic optical sensitivity of the detector.

The optical detection platform 172 may advantageously be utilized to provide information regarding the position of the microlocations 162, interstitial regions 220 and, generally, the placement and positioning of the object to be examined 164. The excitation radiation 180*a* may be supplied via, among others, the scanning system 190, to multiple points on the surface of the object to be examined 164. The excitation radiation 180*h* comprises excitation radiation 180 which has been reflected from the object to be examined 164 and detected at the excitation detector 240 (FIG. 4). Preferably, the multiple points are detected by scanning the excitation radiation 180 over the surface of the object to be examined 164. By receiving, storing and comparing the excitation radiation 180*h* as determined by the excitation detector 240, the received information may be used to form an image of the object to be examined 164. In the preferred embodiment, the received information from the excitation detector 240 is used in conjunction with preentered information regarding the relative position of the microlocations 162 and interstitial regions 220. Since the structure of the object to be examined 164 is known prior to the alignment step, the amount of information required regarding the position of the object to be examined is reduced, and the positional determination may be made more rapidly as compared to the situation where the structure of the object to be examined 164 is unknown. Once the position of the microlocations 162 relative to the optical detection platform 172 is known, the examining of a given microlocation 162 may be performed as described previously in connection with FIGS. 4 and 5. While the microlocations 162 are the preferred object to be imaged by the excitation radiation 180h, other markers, alignment marks or fiducals may be utilized, alone or in combination, to form the imaging. When used herein, position may refer to absolute or relative position, for example, the values of the stepper motors 194 corresponding to a given mirror position may be considered a position (since they indicate where the microlocation is for purposes of illumination and detection).

Figure 6A:
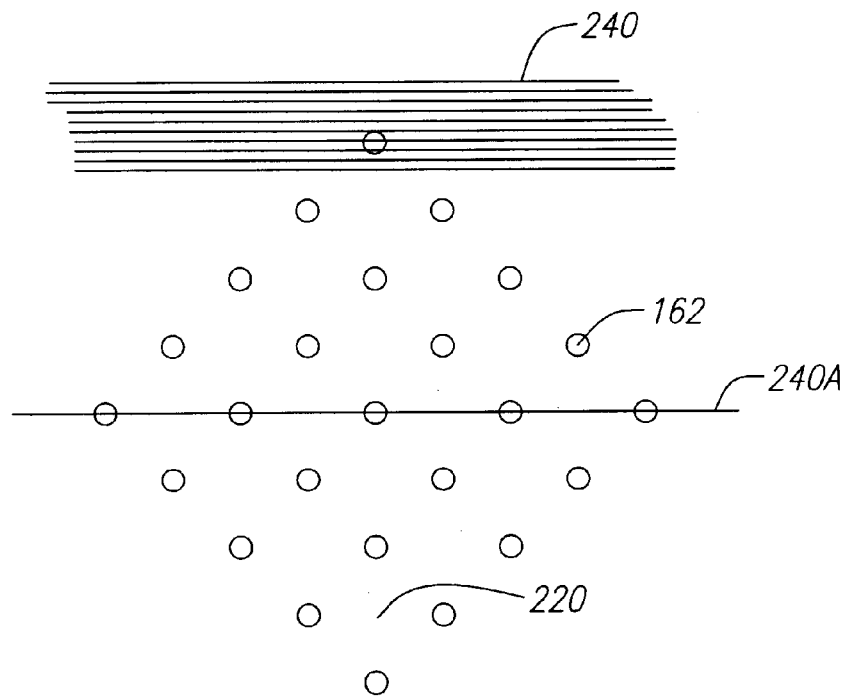
FIG. 6A shows a plan view of an array of microlocators with overlaid scans.
Figure 6B:
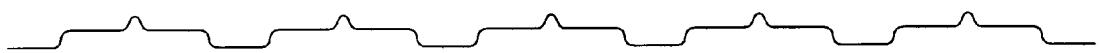
FIG. 6B shows the output of the excitation detector when scanning along line 240a in FIG. 6A.
Figure 1:
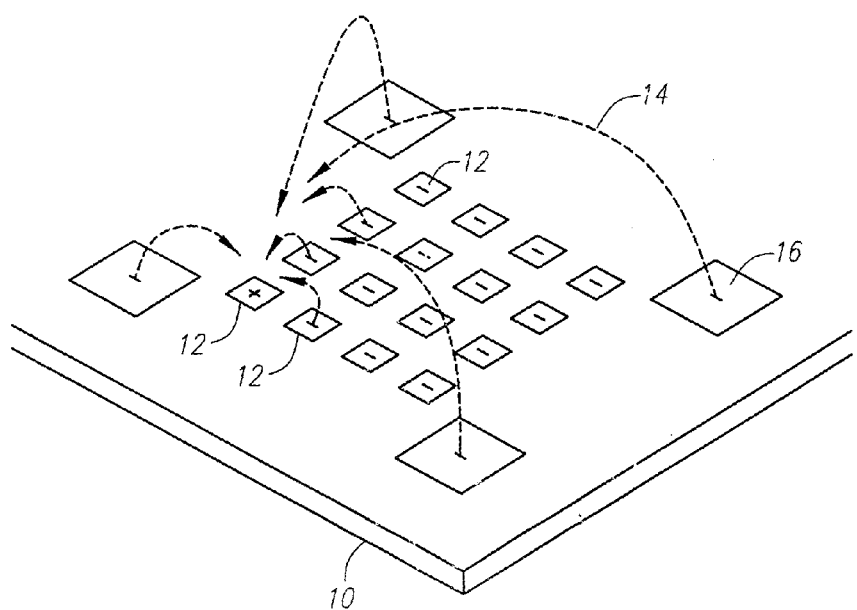
Figure 2:
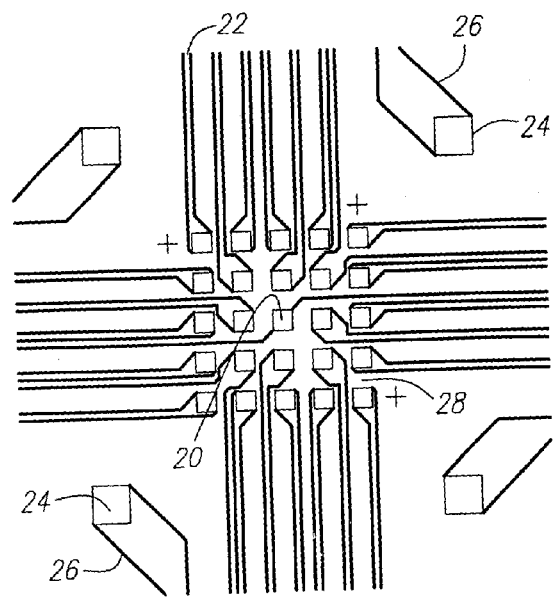
Figure 3:
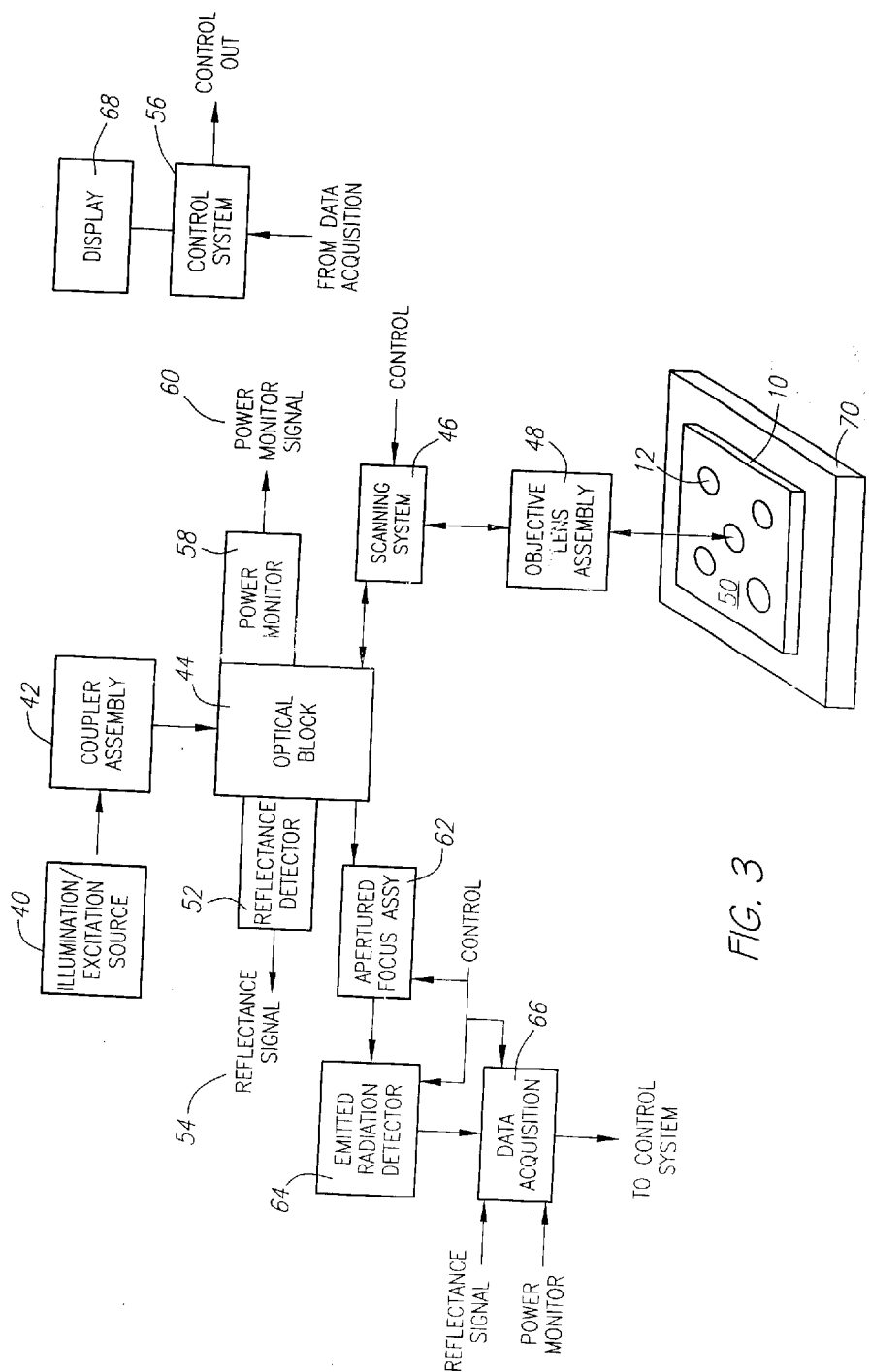

FIGS. 6A and 6B show possible modes of scanning in the preferred method of alignment. FIG. 7A shows an array of microlocations 162 and interstitial areas 220. The scan lines 240 are shown over a portion of FIG. 6A, so as not to obscure the entire figure. Preferably, the entire area in which the array may be located in scanned. However, a lesser region may be scanned consistent with the goals and objects of this invention. In the preferred embodiment, the array of microlocations 162 is oriented such that the scan line 240A would ;can the array along the long dimension of the array. FIG. 6B shows the output from the detector 240 along one scan line (see FIG. 4). The scan in FIG. 6B generally shows relative intensity across the scan 240A in FIG. 6A. By determining the periodicity, the position of the matrix may be determined. While the location of the microlocations 162 may be determined by examining the output of the detector 240 alone, it is advantageously utilized in conjunction with information regarding the structure of the device, such as the size and relative positioning of the microlocations 162.

In the preferred embodiment, the system of this invention utilizes the optical detection platform 172 to both detect the fluorescence 204 from the object under investigation, as well as to detect the excitation radiation 180h which is used to provide positioning information regarding the microlocations 162. In this way, flexibility is provided regarding the mechanical positioning of the microlocations 162 relative to the remainder of the system. In the preferred mode, the scanned excitation radiation 180h is detected by the excitation detector 240, which is provided to the detection system, which preferably in combination with the information regarding the positioning of the microlocations relative to one another, serves to direct the scanning system 190 to directly provide the excitation radiation 180g to the microlocation 162. Through the use of the initial imaging step, the positions of the microlocations 162 may be determined to a degree of precision sufficient to perform the fluorescence detection step by substantially illuminating only a desired microlocation.

When utilized with an APEX system, the signal-to-noise ratio is increased from $10^4$ to times $10^5$ through use of a confocal system, reducing the area of illumination down to the desired imaging location may result in a reduction of scattered light to 1% or less compared to flood illumination, and imaging of that location provides yet another similar decrease in detected scattered radiation, resulting in a reduction of detected radiation from approximately 1/5000 to 1/70,000.

For use with the APEX device, the overall system parameters include that the detector 208 should have a minimum detectable fluorophore density of 0.2 fluorophores per square micron, a minimum optical signal-to-noise ratio of 10:1 at 1 second at 0.2 fluorophores per square micron, a maximum excitation energy of 0.1 microwatt per square micron and a detection resolution of 16 bits ±2, that is, a maximum decimal integer of 65,536 ($2^{16}$) for 4 states ($2^2$) for a resolution with a precision of ±4 parts out of 65,636, or ±0.006% of full scale.

The use of the dual detector system wherein the optical system is utilized to determine the positions of the microlocation and th en, based upon that positional information, is utilized to provide excitation radiation to a given microlocation, provides significantly increased alignment characteristics relative to pure mechanical systems. Whereas the mechanical positioning in the combined system provides for a positioning accuracy of ±500 microns in the x and y directions, utilizing the optical position detection system of this invention permits an alignment accuracy of approximately 1 micron.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

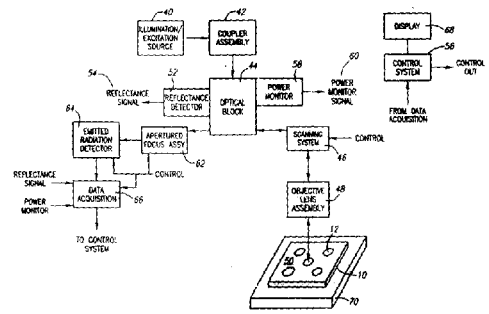

We claim:

1. A system for optical detection of emitted radiation from one or more microlocations separated by interstitial regions on an object to be examined, comprising:

a light source providing excitation radiation characterized in that the diameter of the excitation radiation when illuminating the object is of the same diameter or less than the diameter of the microlocation to be examined, a confocal scanning system adapted to receive the excitation radiation and direct it to the object and to provide reflected radiation and emitted radiation from the microlocation, a first detector adapted to receive the reflected radiation and generate an output, a position detection system configured to receive the output of the first detector and based on the output determine position information regarding one or more microlocations, a control system coupled to the position detection system which utilizes the position information to cause the confocal scanning system to direct excitation radiation to substantially only one microlocation at a time and substantially not to the interstitial regions on the object, wherein the location of the microlocation is predetermined based on position information, and a second detector operatively positioned to receive the emitted radiation from the microlocation.

2. The system of claim 1 wherein the excitation source is a laser.

3. The system of claim 2 wherein the laser is a single laser source.

4. The system of claim 1 wherein the scanning system is an x-y scanning system.

5. The system of claim 4 wherein the x-y scanning system includes a mirror adapted to reflect the excitation radiation, the reflected radiation and the emitted radiation.

6. The system of claim 1 wherein the second detector further includes an aperture.

7. The system of claim 6 wherein the aperture comprises a pinhole aperture.

8. The system of claim 7 wherein the pinhole aperture corresponds to a microlocation with a diameter in the range from substantially 20 microns to 80 microns.

9. The system of claim 8 wherein the pinhole aperture corresponds to a microlocation with a diameter of substantially 50 microns.

10. The system of claim 1 further including a focusing motor which is capable of moving the position detection system and the aperture.

11. The system of claim 1 further including a rejection filter disposed between the confocal scanning system and the second detector.

12. The system of claim 11 wherein the rejection filter rejects excitation radiation to a factor of $10^7$.

13. The system of claim 11 wherein the rejection filter rejects excitation radiation to a factor of $10^{10}$.

14. The system of claim 1 further including a data acquisition system.

15. The system of claim 1 further including a display.

16. The system of claim 1 further including a laser power monitor positioned to receive excitation radiation and output an indication of laser power.

17. The system of claim 16 wherein the output of the laser power monitor is connected to the control system.

18. The system of claim 1, wherein the position information is x-y position information.

19. A system for optical detection of emitted radiation from at least one microlocation on an object including one or more microlocations to be examined, comprising:

at least one light source providing excitation radiation characterized in that the diameter of the excitation radiation when illuminating the object is of the same diameter or less than the diameter of the microlocation to be examined, a confocal scanning system adapted to receive excitation energy and selectively direct the excitation energy to at least one microlocation thereon and to provide reflected radiation from the microlocation and emitted radiation from the microlocation, a first detector adapted to receive the reflected radiation and generate an output, a position detection system configured to receive the output of the first detector and based on the output determine position information regarding at least one microlocation, a control system coupled to the position detection system which causes, for each microlocation to be examined, the confocal scanning system to generally align with the microlocation, direct excitation radiation to the microlocation only when the confocal scanning system is aligned with the microlocation, and collect emitted radiation from the microlocation before moving to a next microlocation to be examined, and a second detector operatively positioned to receive the emitted radiation from the microlocation.

20. The system of claim 19 wherein the excitation source is a laser.

21. The system of claim 19 wherein the scanning system is an x-y scanning system.

22. The system of claim 19 wherein the second detector includes an aperture through which the emitted radiation travels.

23. The system of claim 22 wherein the aperture comprises a pinhole aperture.

24. The system of claim 23 wherein the pinhole aperture corresponds to a microlocation with a diameter in the range from substantially 20 microns to 80 microns.

25. The system of claim 19 further including a laser power monitor positioned to receive excitation radiation and output an indication of laser power.

26. The system of claim 19, wherein the control system uses the position information to selectively control the order in which microlocations are examined.

27. A system for optical detection of emitted radiation from microlocations on an object to be examined, comprising:

a light source configured to generate light, a confocal scanning system adapted to receive the light and direct it to the object and to receive excitation radiation and direct it to one or more microlocations and to provide reflected radiation and emitted radiation from the microlocation, an excitation radiation source configured to generally only direct excitation radiation to the confocal scanning system when the confocal scanning system is aligned with a microlocation, the excitation radiation characterized in that the diameter of the excitation radiation when illuminating the microlocation is of the same diameter or less than the diameter of the microlocation to be examined, a first detector adapted to receive the reflected radiation and generate an output, a position detection system configured to receive the output of the first detector and based on the output determine position information regarding one or more microlocations, a control system coupled to the position detection system which causes the confocal scanning system to selectively align with the one or more microlocations based on the position information, wherein the one or more microlocations in sum are a subset of all the microlocations available for scanning on the object, and a second detector operatively positioned to receive the emitted radiation from the one or more microlocations, the second detector characterized in that the diameter of a microlocation examined by the detector is less than or equal to the diameter of the excitation radiation.

28. The system of claim 27 wherein the scanning system is an x-y scanning system.

29. The system of claim 27 further including a focusing motor.

30. The system of claim 27 further including a laser power monitor positioned to receive excitation radiation and output an indication of laser power.

31. A system for optical detection of emitted radiation from microlocations on an object to be examined, comprising:

a light source providing excitation radiation characterized in that the diameter of the excitation radiation when illuminating the microlocation is of the same diameter or less than the diameter of the microlocation to be examined, a confocal scanning system adapted to receive the excitation radiation and direct it to the microlocation and to provide reflected radiation and emitted radiation from the microlocation, a first detector adapted to receive the reflected radiation and a position detection system, the first detector having an output connected to a position detection system, a second detector operatively positioned to receive the emitted radiation from the microlocation, the detector characterized in that the diameter examined by the detector is less than or equal to the diameter of the excitation radiation, a control system coupled to the position detection system which causes the confocal scanning system to direct excitation radiation to a specific microlocation, and a rejection filter disposed between the confocal scanning system and the second detector, wherein the rejection filter rejections excitation radiation to a factor of $10^7$.

32. A system for optical detection of emitted radiation from microlocations on an object to be examined, comprising:

a light source providing excitation radiation characterized in that the diameter of the excitation radiation when illuminating the microlocation is of the same diameter or less than the diameter of the microlocation to be examined, a confocal scanning system adapted to receive the excitation radiation and direct it to the microlocation and to provide reflected radiation and emitted radiation from the microlocation, a first detector adapted to receive the reflected radiation and a position detection system, the first detector having an output connected to a position detection system, a second detector operatively positioned to receive the emitted radiation from the microlocation, the detector characterized in that the diameter examined by the detector is less than or equal to the diameter of the excitation radiation, a control system coupled to the position detection system which causes the confocal scanning system to direct excitation radiation to a specific microlocation, and a rejection filter disposed between the confocal scanning system and the second detector, wherein the rejection filter rejections excitation radiation to a factor of $10^{10}$.

33. A system for optical detection of emitted radiation from microlocations on an object to be examined, comprising:

a light source providing excitation radiation characterized in that the diameter of the excitation radiation when illuminating the microlocation is of the same diameter or less than the diameter of the microlocation to be examined, a confocal scanning system adapted to receive the excitation radiation and direct it to the microlocation and to provide reflected radiation and emitted radiation from the microlocation, a first detector adapted to receive the reflected radiation and a position detection system, the first detector having an output connected to a position detection system, a second detector operatively positioned to receive the emitted radiation from the microlocation, the detector characterized in that the diameter examined by the detector is less than or equal to the diameter of the excitation radiation, a control system coupled to the position detection system which causes the confocal scanning system to direct excitation radiation to a specific microlocation, and a laser power monitor positioned to receive excitation radiation and output an indication of laser power.

34. A system for optical detection of emitted radiation from microlocations on an object to be examined, comprising:

a light source providing excitation radiation characterized in that the diameter of the excitation radiation when illuminating the microlocation is of the same diameter or less than the diameter of the microlocation to be examined, a confocal scanning system adapted to receive the excitation radiation and direct it to the microlocation and to provide reflected radiation and emitted radiation from the microlocation, a first detector adapted to receive the reflected radiation and a position detection system, the first detector having an output connected to a position detection system, a second detector operatively positioned to receive the emitted radiation from the microlocation, the detector characterized in that the diameter examined by the detector is less than or equal to the diameter of the excitation radiation, a control system coupled to the position detection system which causes the confocal scanning system to direct excitation radiation to a specific microlocation, and a laser power monitor connected to the control system and positioned to receive excitation radiation and output an indication of laser power.

* * * * *

UNITED STATES PATENT AND TRADEMARK OFFICE
CERTIFICATE OF CORRECTION

PATENT NO. : 6,309,601 B1
DATED : October 30, 2001
INVENTOR(S) : Robert D. Juncosa et al.

It is certified that error appears in the above-identified patent and that said Letters Patent is hereby corrected as shown below:

<u>Title page,</u>
Title page should be deleted to be replaced with the attached title page.

<u>Drawings,</u>
Drawing sheets consisting of Figs. 1 and 3 should be deleted to be replaced with the drawing sheets, consisting of Figs. 1 and 3 as shown on the attached pages.

<u>Column 1,</u>
Lines 11 and 12, change "now, issued," to -- now issued --.
Line 40, change "spring" to -- Spring --.

<u>Column 4,</u>
Line 2, change "a x-y" to -- an x-y --.

<u>Column 6,</u>
Lines 29 and 41, change "optic al" to -- optical --.
Line 46, change "provides" to -- provided --.

<u>Column 7,</u>
Line 9, change "optional" to -- optical --.
Lines 31 and 32, change "beam splitter" to -- beamsplitter --.

<u>Column 10,</u>
Line 11, change "microlocations 220" to -- microlocations 162 --.
Line 33, change "regions 38" to -- regions 28 --.

<u>Column 11,</u>
Line 20, change ":can" to -- scan --.

UNITED STATES PATENT AND TRADEMARK OFFICE
CERTIFICATE OF CORRECTION

PATENT NO. : 6,309,601 B1
DATED : October 30, 2001
INVENTOR(S) : Robert D. Juncosa et al.

It is certified that error appears in the above-identified patent and that said Letters Patent is hereby corrected as shown below:

Column 12,
Line 3, change "th en" to -- then --.

Signed and Sealed this

Twenty-fourth Day of December, 2002

JAMES E. ROGAN
*Director of the United States Patent and Trademark Office*

(12) United States Patent
Juncosa et al.

(10) Patent No.: US 6,309,601 B1
(45) Date of Patent: *Oct. 30, 2001

(54) SCANNING OPTICAL DETECTION SYSTEM

(75) Inventors: Robert D. Juncosa, Mission Viejo; William F. Butler, Carlsbad; Lei Wu, San Diego, all of CA (US); Robert H. Cormack, Boulder, CO (US)

(73) Assignee: Nanogen, Inc., San Diego, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/846,876

(22) Filed: May 1, 1997

Related U.S. Application Data

(63) Continuation-in-part of application No. 08/304,657, filed on Sep. 9, 1994, now Pat. No. 5,632,957, which is a continuation-in-part of application No. 08/271,882, filed on Jul. 7, 1994, now Pat. No. 6,017,969, which is a continuation-in-part of application No. 08/146,504, filed on Nov. 1, 1993, now Pat. No. 5,605,662.

(51) Int. Cl.[7] ............... G01N 15/00; G01N 1/00; G01N 33/53; C12Q 1/68
(52) U.S. Cl. ............... 422/68.1; 422/50; 422/69; 422/82.05; 422/82.08; 422/82.09; 435/6; 435/7.1; 436/501
(58) Field of Search ............... 422/50, 68.1, 69, 422/82.05, 82.08, 82.09; 435/6, 7.1; 436/501; 935/77, 78, 88

(56) References Cited

U.S. PATENT DOCUMENTS

| | | |
|---|---|---|
| 4,555,731 | 11/1985 | Zinchuk .................. 358/209 |
| 4,572,668 | 2/1986 | Auth ...................... 356/318 |
| 4,707,235 | 11/1987 | Englert et al. ........... 204/182.8 |
| 4,881,812 | 11/1989 | Ohkubo et al. ........... 356/344 |
| 5,096,807 | 3/1992 | Leaback .................. 435/6 |
| 5,192,980 | 3/1993 | Dixon et al. ............. 356/326 |
| 5,296,703 | 3/1994 | Tsien ..................... 250/235 |
| 5,324,401 | 6/1994 | Yueng et al. ............. 204/180.1 |
| 5,381,224 | 1/1995 | Dixon et al. ............. 356/72 |
| 5,578,832 | 11/1996 | Trulson et al. ........... 250/458.1 |
| 5,631,734 | 5/1997 | Stern et al. ............. 356/317 |

OTHER PUBLICATIONS

"Theory and Practice of Scanning Optical Microscopy", Tony Wilson and Colin Sheppard, Academic Press, 1984 (ISBN-0-12-757760-2).

Scanning Laser Microscopy Lab, Web Site print-out, http://www.science.uwaterloo.ca/research_groups/confocal (1997).

*Primary Examiner*—Ardin H. Marschel
(74) *Attorney, Agent, or Firm*—Lyon & Lyon LLP

(57) ABSTRACT

An optical detection system is adapted for detection of biological reactions. An excitation source illuminates a portion of an object to be examined, the portion preferably comprising one microlocation out of an array of microlocations. An intervening optical detection platform serves to direct the excitation radiation to the portion of the object to be illuminated. A detector receives the emitted radiation from the object to be examined, the detector being characterized in that the diameter of the region examined by the detector is the same as or smaller than the diameter of the illuminated region, and comprises less than the entire surface of the object to be examined, and most preferably images a whole or a part of a single microlocation. In operation, a microscopy system is formed in which the excitation radiation is substantially in focus at the surface of the object to be examined. In one aspect of this invention, the optical detection platform includes an excitation detector that measures reflected excitation radiation from the object to be examined. This information is compared to prestored information regarding the location of the microlocations and interstitial regions on the object to be examined, whereby alignment information is obtained. The excitation radiation may then be precisely directed to a given microlocation or portion thereof to perform the examining through the system.

34 Claims, 5 Drawing Sheets